(12) United States Patent
Nadkarni et al.

(10) Patent No.: US 10,507,296 B2
(45) Date of Patent: Dec. 17, 2019

(54) SYSTEM AND METHOD FOR TEACHING, PRACTICING AND PERFORMING EFFECTIVE RESCUE BREATHING

(71) Applicants: The Children's Hospital of Philadelphia, Philadelphia, PA (US); Nihon Kohden Corporation, Shinjuku-ku, Tokyo (JP)

(72) Inventors: Vinay Nadkarni, Media, PA (US); Akira Nishisaki, Philadelphia, PA (US); Elizabeth Foglia, Swarthmore, PA (US); Dana Niles, Merion, PA (US); Fumihiko Takatori, Wynnewood, PA (US)

(73) Assignees: The Children's Hospital of Philadelphia, Philadelphia, PA (US); Nihon Kohden Corporation, Tokyo (JP)

( * ) Notice: Subject to any disclaimer, the term of this patent is extended or adjusted under 35 U.S.C. 154(b) by 281 days.

(21) Appl. No.: 15/517,322

(22) PCT Filed: Oct. 7, 2015

(86) PCT No.: PCT/US2015/054384
§ 371 (c)(1),
(2) Date: Apr. 6, 2017

(87) PCT Pub. No.: WO2016/057612
PCT Pub. Date: Apr. 14, 2016

(65) Prior Publication Data
US 2018/0333548 A1    Nov. 22, 2018

Related U.S. Application Data

(60) Provisional application No. 62/060,856, filed on Oct. 7, 2014.

(51) Int. Cl.
*A61M 16/00* (2006.01)
*A61M 16/06* (2006.01)
(Continued)

(52) U.S. Cl.
CPC ....... *A61M 16/0051* (2013.01); *A61B 5/0053* (2013.01); *A61B 5/097* (2013.01);
(Continued)

(58) Field of Classification Search
CPC ............. A61M 16/00; A61M 16/0003; A61M 16/0048; A61M 16/0051; A61M 16/084;
(Continued)

(56) References Cited

U.S. PATENT DOCUMENTS

| 5,195,896 A | 3/1993 | Sweeney |
| 5,289,819 A * | 3/1994 | Kroger .................. A62B 27/00 128/200.24 |

(Continued)

FOREIGN PATENT DOCUMENTS

DE    102008028662 A1 * 12/2008    ............... A61B 5/08

OTHER PUBLICATIONS

International Search Report and Written Opinion for International Application No. PCT/US2015/054384, dated Jan. 11, 2016—9 Pages.

*Primary Examiner* — Joseph D. Boecker
(74) *Attorney, Agent, or Firm* — RatnerPrestia

(57) ABSTRACT

A system includes: a first sensor configured to measure one of a ventilatory volume, a concentration of gas, a respiratory rate and a respiratory pressure; a second sensor configured to measure a pressure associated with a mask adapted to be attached to a human patient or a mannequin; a processor configured to analyze a measurement value of the first sensor and a measurement value of the second sensor; and an output unit connected to the processor, and configured to
(Continued)

output, based on a result of the analysis of the processor, at least one of: a condition of the mask adapted to be attached to the human patient or the mannequin; and a condition of the human patient or the mannequin.

18 Claims, 10 Drawing Sheets

(51) Int. Cl.
 *G09B 23/28* (2006.01)
 *A61B 5/00* (2006.01)
 *A61B 5/097* (2006.01)
(52) U.S. Cl.
 CPC ......... *A61B 5/744* (2013.01); *A61M 16/0084* (2014.02); *A61M 16/021* (2017.08); *A61M 16/06* (2013.01); *G09B 23/288* (2013.01); A61B 5/746 (2013.01); A61M 2016/0027 (2013.01); A61M 2016/0033 (2013.01); A61M 2205/15 (2013.01); A61M 2205/332 (2013.01); A61M 2205/3344 (2013.01); A61M 2205/502 (2013.01); A61M 2205/583 (2013.01); A61M 2230/42 (2013.01); A61M 2230/432 (2013.01)
(58) Field of Classification Search
 CPC .............. A61M 16/021; A61M 16/022; A61M 16/024; A61M 16/06; A61M 2016/0027; A61M 2016/0033; A61M 2205/3344; A61M 2205/583; A61M 2230/40; A61M 2230/42; A61M 2230/43; A61M 2230/432; G09B 23/288; A61B 5/0053; A61B 5/087; A61B 5/091; A61B 5/097; A61B 5/742; A61B 5/7425; A61B 5/743; A61B 5/744; A61B 5/746
 See application file for complete search history.

(56) References Cited

U.S. PATENT DOCUMENTS

| | | |
|---|---|---|
| 5,377,314 A | 12/1994 | Bates |
| 6,135,106 A | 10/2000 | Dirks |
| 2004/0163648 A1* | 8/2004 | Burton ............... A61B 5/04085 128/204.21 |
| 2005/0085799 A1* | 4/2005 | Luria ................... A61B 5/6803 606/1 |
| 2006/0111749 A1* | 5/2006 | Westenskow ......... A61M 16/00 607/5 |
| 2008/0214948 A1* | 9/2008 | Myklebust ............. A61B 5/087 600/538 |
| 2010/0175699 A1 | 7/2010 | Varney |
| 2011/0271959 A1* | 11/2011 | Jensen .................. A61M 16/06 128/204.23 |
| 2012/0240933 A1* | 9/2012 | Haas .................... A61M 16/06 128/204.21 |
| 2013/0211214 A1* | 8/2013 | Olsen ..................... A61B 5/742 600/316 |
| 2013/0228180 A1 | 9/2013 | Ahmad |
| 2013/0263857 A1* | 10/2013 | Ahmad ................. A61M 16/00 128/205.23 |
| 2013/0267863 A1* | 10/2013 | Orr ...................... A61B 5/0836 600/532 |
| 2014/0364758 A1* | 12/2014 | Schindhelm ........... A61B 5/082 600/531 |
| 2017/0049978 A1* | 2/2017 | Berg ................. A61M 16/0078 |

* cited by examiner

FIG. 8A
FIG. 8B
FIG. 8C
FIG. 8D
FIG. 9A
FIG. 9B
FIG. 9C

SYSTEM AND METHOD FOR TEACHING, PRACTICING AND PERFORMING EFFECTIVE RESCUE BREATHING

RELATED APPLICATIONS

This application is the United States National Phase of International Application No. PCT/US2015/054384, filed Oct. 7, 2015, which claims the benefit of priority of U.S. Provisional Application No. 62/060,856, filed Oct. 7, 2014. The contents of International Application No. PCT/US2015/054384 and U.S. Provisional Application No. 62/060,856 are incorporated by reference herein in their entireties.

FIELD

The present invention relates generally to positive pressure ventilation, and more particularly to systems and methods for teaching, practicing and performing proper techniques for effective rescue breathing.

BACKGROUND

Birth asphyxia is a major cause of newborn death and brain injury. When a newborn is unable to breathe, or has limited ability to breathe, medical personnel must act quickly. Typically, medical personnel will perform rescue breathing (sometimes referred to as "basic resuscitation", "manual resuscitation", or "bag-and-mask" rescue breathing). In general terms, rescue breathing is a procedure in which positive pressure ventilation is used to help a patient breathe. In one type of procedure, a bag-valve mask is placed over the patient's nose and mouth. The "bag" portion of the bag-valve mask consists of a flexible chamber that is compressed or squeezed by hand to force gas out of a first end of the bag and into the patient's lungs. When the bag is released, the bag self-inflates with either ambient air or oxygen gas that enters through a second end of the bag. While the bag self-inflates, the patient's lungs can expel gas to the ambient environment.

Medical professionals and emergency personnel must have proper training to perform effective rescue breathing. Effective rescue breathing is particularly challenging when the patient is a newborn. Many times, medical personnel monitor the newborn's rescue breathing by confirming chest wall movement. Confirming chest wall movement can be very difficult, however, even if the clinician is very experienced.

Effective rescue breathing is also made difficult by the number of parameters that must be monitored at one time. A clinician must squeeze the bag at an appropriate rate to provide an adequate respiratory rate. Therefore, the respiratory rate must be monitored and controlled. The clinician must also deliver an appropriate volume of air or gas into the patient's lungs. Too little volume will deliver an insufficient amount of oxygen, while too much volume can be unsafe for the patient. As such, tidal volume must be monitored and controlled. To complicate matters further, the clinician must also maintain a proper seal between the mask and the patient's face to ensure that gas being squeezed from the bag is delivered to the patient's lungs. A leak can be very difficult to detect and locate for the obvious reason that the leak is not visible.

Monitoring so many variables at the same time can be extremely difficult, particularly when only one person performs the rescue breathing. Often times, two individuals carry out the rescue breathing procedure so that the responsibilities are divided. One person might focus on holding the mask to maintain a proper seal, while the other person focuses on squeezing the bag to maintain an appropriate respiratory rate and volume. Unfortunately, it is not always possible to have two individuals on hand during a rescue breathing event. Even when two individuals are available, it is still very difficult to monitor so many parameters, identify when a problem occurs and address the problem in a short amount of time.

SUMMARY

In one beneficial and advantageous aspect of the invention, a system includes a first sensor and a second sensor. The first sensor is configured to measure one of a ventilatory volume, a concentration of gas, a respiratory rate and a respiratory pressure. The second sensor is configured to measure a pressure associated with a mask adapted to be attached to a human patient or a mannequin. A processor is configured to analyze a measurement value of the first sensor and a measurement value of the second sensor. An output unit is connected to the processor, with the output unit being configured to output, based on a result of the analysis of the processor, at least one of a condition of the mask adapted to be attached to the human patient or the mannequin, and a condition of the human patient or the mannequin.

In another beneficial and advantageous aspect of the invention, the system includes an adapter to which the first sensor is attached.

In another beneficial and advantageous aspect of the invention, the second sensor is located on the mask.

In another beneficial and advantageous aspect of the invention, the second sensor is located on the mannequin.

In another beneficial and advantageous aspect of the invention, an alarm unit is configured to output an alarm in accordance with the measurement value of the first sensor.

In another beneficial and advantageous aspect of the invention, the output unit is configured to output an instruction when the alarm unit outputs the alarm.

In another beneficial and advantageous aspect of the invention, the system includes the mask which is attachable to the human patient or the mannequin.

In another beneficial and advantageous aspect of the invention, the output unit includes a display unit configured to display, based on the result of the analysis of the processor, the at least one of: the condition of the mask adapted to be attached to the human patient or the mannequin; and the condition of the human patient or the mannequin.

In another beneficial and advantageous aspect of the invention, a system includes a first sensor. The first sensor is configured to measure a first one of parameters including a ventilatory volume, a concentration of gas, a respiratory rate and a respiratory pressure. A processor is configured to analyze a measurement value of the first sensor. An output unit is connected to the processor and configured to output, based on a result of the analysis of the processor, at least one of: a condition of a mask adapted to be attached to a human patient or a mannequin; and a condition of the human patient or the mannequin.

In another beneficial and advantageous aspect of the invention, the output unit includes a display unit configured to display an image in which an element representing the condition of the mask and an element representing the condition of the human patient or the mannequin are overlapped with each other.

In another beneficial and advantageous aspect of the invention, the display unit is configured to concurrently display a first image of the element representing the condition of the mask, a second image of the element representing the condition of the human patient or the mannequin, and a third image in which the element representing the condition of the mask is overlapped on the element representing the condition of the human patient or the mannequin.

In another beneficial and advantageous aspect of the invention, a second sensor is configured to measure a second one of the parameters, wherein the first one of the parameters measured by the first sensor is different from the second one of the parameters measured by the second sensor, and the processor is configured to analyze the measurement value of the first sensor and a measurement value of the second sensor.

In another beneficial and advantageous aspect of the invention, a third sensor is configured to measure a pressure associated with the mask adapted to be attached to the human patient or the mannequin, wherein the processor is configured to analyze the measurement value of the first sensor, the measurement value of the second sensor, and a measurement value of the third sensor.

In another beneficial and advantageous aspect of the invention, the third sensor includes a plurality of sensors arranged on a plurality of positions and configured to measure pressures at the plurality of positions, respectively, and the output unit is configured to further output information related to the pressures of the plurality of positions.

In another beneficial and advantageous aspect of the invention, a second sensor is configured to measure a pressure associated with the mask adapted to be attached to the human patient or the mannequin, wherein the processor is configured to analyze the measurement value of the first sensor and a measurement value of the second sensor.

In another beneficial and advantageous aspect of the invention, the second sensor includes a plurality of sensors arranged on a plurality of positions and configured to measure pressures at each of the plurality of positions, respectively, and the output unit is configured to further output information related to the pressures at each of the plurality of positions.

In another beneficial and advantageous aspect of the invention, the first sensor is configured to measure the ventilatory volume, and the element representing the condition of the mask is obtained based on the ventilatory volume measured by the first sensor.

In another beneficial and advantageous aspect of the invention, the element representing the condition of the human patient or the mannequin is obtained based on the first one of the parameters measured by the first sensor.

In another beneficial and advantageous aspect of the invention, the first sensor is configured to measure the ventilatory volume, and the element representing the condition of the mask is obtained based on the ventilatory volume measured by the first sensor or the pressure associated with the mask measured by the second sensor.

In another beneficial and advantageous aspect of the invention, the element representing the condition of the human patient or the mannequin is obtained based on the first one of the parameters measured by the first sensor or the pressure associated with the mask measured by the second sensor.

In another beneficial and advantageous aspect of the invention, a positive pressure ventilation mask includes a first sensor configured to measure one of a ventilatory volume, a concentration of gas, a respiratory rate and a respiratory pressure, and a second sensor configured to measure a pressure condition associated with the positive pressure ventilation mask.

In another beneficial and advantageous aspect of the invention, the second sensor is configured to measure a pressure exerted by the positive pressure ventilation mask on a human patient or a mannequin to which the positive pressure ventilation mask is attached.

In another beneficial and advantageous aspect of the invention, the second sensor is configured to measure at least one pressure inside the positive pressure ventilation mask during operation of the positive pressure ventilation mask.

In another beneficial and advantageous aspect of the invention, the at least one pressure in the positive pressure ventilation mask includes a peak inspiratory pressure (PIP) or a positive end expiratory pressure (PEEP) during operation of the positive pressure ventilation mask.

In another beneficial and advantageous aspect of the invention, the positive pressure ventilation mask includes an adapter to which the first sensor is attached.

In another beneficial and advantageous aspect of the invention, an apparatus for teaching and practicing positive pressure ventilation includes a mannequin having a face area for attaching a positive pressure ventilation mask and at least one sensor for measuring a pressure exerted on the face area.

In another beneficial and advantageous aspect of the invention, the at least one sensor includes a plurality of sensors spatially arranged on the face area.

In another beneficial and advantageous aspect of the invention, the at least one sensor comprises a pressure transducer.

In another beneficial and advantageous aspect of the invention, the mannequin includes a chamber for receiving air under positive pressure.

In another beneficial and advantageous aspect of the invention, the mannequin includes an inlet for allowing air under positive pressure into the chamber.

In another beneficial and advantageous aspect of the invention, the inlet is the only pathway for air into or out of the chamber, such that the chamber cannot discharge or leak air when air is introduced through the inlet.

In another beneficial and advantageous aspect of the invention, the at least one sensor includes a plurality of sensors spaced around the inlet.

In another beneficial and advantageous aspect of the invention, the mannequin includes at least one zone located in the face area, the at least one zone aligned with the at least one sensor.

BRIEF DESCRIPTION OF THE DRAWINGS

FIGS. 8A to 8D are views showing images of elements representing attachment conditions of a mask;

FIGS. 9A to 9C are views showing images of elements representing conditions of a human patient or a mannequin.

DETAILED DESCRIPTION

Although the invention is illustrated and described herein with reference to specific embodiments, the invention is not intended to be limited to the embodiments shown. Rather, the invention encompasses various modifications and combinations of the details shown.

Systems and methods in accordance with the invention resolve the risks and drawbacks associated with conventional rescue breathing techniques by utilizing real time monitoring of different parameters, and by coaching the clinician based on those parameters. Coaching is accomplished by providing the clinician with real time data, visual signals and/or audio signals. Real time data enables the clinician to easily monitor all of the critical parameters, know precisely when a problem occurs, identify the specific cause of the problem, and immediately correct the problem. There are many factors that can prevent proper rescue breathing, such as insufficient positive pressure and/or leakage through the mask. By coaching the clinician, the present invention allows the clinician to identify a problem and take corrective action in a much shorter time than without coaching. This ability to rapidly identify and correct problems can save precious seconds and save a patient's life.

In addition to coaching the clinician, the present invention can be used in a training context to teach clinicians the proper skills for performing effective rescue breathing. Moreover, the present invention can be used to help clinicians practice and repeat the techniques that they learn, and test their ability to perform effective rescue breathing.

Systems, apparatuses and methods in accordance with the invention can be used in a clinical setting on patients of all ages, including infants, young children, adolescents and adults. In addition, systems, apparatuses and methods in accordance with the invention can be used in a training context with masks, mannequins and other components being appropriately sized to simulate rescue breathing techniques on patients of all ages, including infants, young children, adolescents and adults.

Figure 1:
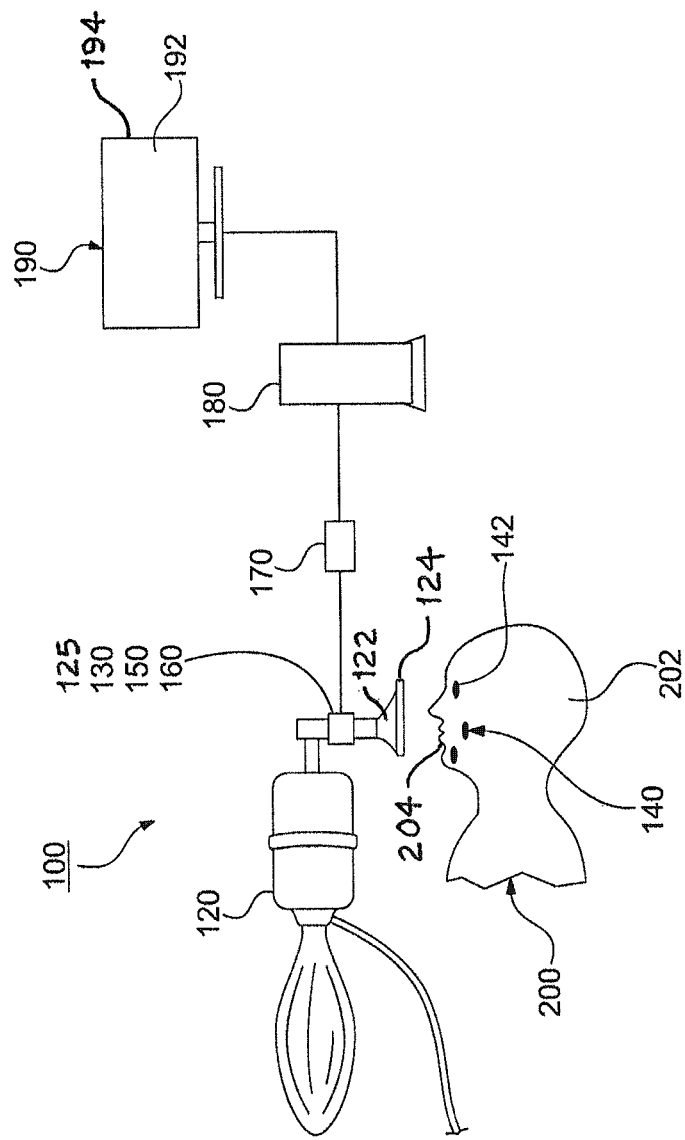
FIG. 1 is a schematic illustration of a system in accordance with one exemplary embodiment.

In one embodiment, a system utilizes a mannequin that the clinician can use to perform a simulated rescue breathing procedure. FIG. 1 is a schematic illustration of one system 100 for teaching and practicing positive pressure ventilation. System 100 includes a positive pressure ventilation mask or bag-valve mask 120. Mask 120 can be an actual bag-valve mask approved for use in actual rescue breathing procedures. Where the mask is approved for use in actual rescue breathing procedures, the mask can be used either on a mannequin or on an actual patient. In systems that are only used for training purposes, and not actual clinical use, the mask need not be approved for clinical use, and can have configurations or modifications that are adapted for instructional use.

Mask 120 is equipped with one or more sensors to monitor different parameters during a simulated or actual rescue breathing procedure, as will be explained. The one or more sensors are connected to a receiver 170 that receives data from the sensors in real time.

Data collected by receiver 170 is sent to a processor 180. It is noted that systems in accordance with the invention need not have a receiver and a processor that are separate components, as alternative arrangements are contemplated. For example, systems in accordance with the invention can feature a processor with an integrated receiver, or a processor that is otherwise directly coupled to sensors. In system 100, processor 180 is connected to an output unit that includes a display monitor 190 with a screen 192 operable to display one or more parameters that are being monitored. Processor 180 may be a conventional computer or a component within a conventional computer. In addition, processor 180 can be in the form of, or include, a microprocessor, a microcontroller and/or a field-programmable gate array. Other suitable types of processors will be understood by one of ordinary skill in the art from the description herein.

Systems in accordance with the invention can include a number of different components, as will be described herein, which can be electrically connected with one another using wired connections or wireless connections. For example, sensors used in accordance with the invention can be electrically connected to receiver 170 with one or more wired connections or wireless connections. The selection of wired connections versus wireless connections can depend on many factors including, but not limited to, the location of the sensors and how they are arranged relative to other components. For example, sensors that are attached to or located on a bag-valve mask, as will be described, can connect to the receiver with wireless connections to avoid complications caused by tangled wires around the patient or mannequin. Other components in accordance with the invention, including but not limited to processor 180 and display unit 190, can also be interconnected with one another and to other components using any combination of wired connections and wireless connections. Individual components and systems described and illustrated herein can utilize any combination of wired connections and wireless connections to connect to and interact with one another. Wireless connections are especially advantageous and contemplated for systems that are monitored and/or operated by portable external devices. Therefore, systems in accordance with invention include partially or fully wireless systems that can be monitored and/or operated by portable devices, including but not limited to smart phones, tablets and lap top computers.

System 100 includes a first sensor 130 for measuring a concentration of carbon dioxide in gas being ventilated through the mask, when the mask is used in an actual rescue breathing procedure. First sensor 130 is in the form of a capnometer attached to an adapter 125. Adapter 125 is configured to be attached to mask 120, forming a ventilation passage. Capnometer is connected through a side of the adapter 125 and positioned in the ventilation passage to measure carbon dioxide concentration.

Systems in accordance with the invention preferably include an additional sensor to monitor the integrity of the mask seal. More preferably, the system includes multiple sensors to monitor the integrity of the mask seal at different locations. For example, system 100 includes a second sensor 140 made up of a plurality of pressure transducers 142. Pressure transducers 142 are configured to measure the integrity of the seal between mask 120 and the patient or mannequin. Each pressure transducer is configured to measure a pressure exerted by the mask against one area or zone around the nose and mouth of the patient or mannequin. Each pressure transducer 142 sends a pressure measurement for its particular zone to receiver 140 and processor 180. Processor 180 is configured to display pressure measurements for each zone in real time on display monitor 190, thereby informing the clinician whether or not adequate pressure is being maintained on the mask to ensure an airtight seal.

Systems in accordance with the invention are designed to help clinicians learn to maintain airtight seals. Although it is highly preferable to avoid leaks altogether, a small amount of leakage around the mask can be tolerated if other parameters indicate that effective rescue breathing is being performed. In cases where a small leak is detected, the clinician can monitor the readings from the pressure transducers 140 and watch for changes in pressure that could signal a larger leak.

Although not required, systems in accordance with the invention can be manufactured and distributed with a training mannequin for simulating a rescue breathing procedure. Alternatively, systems in accordance with the invention can be manufactured and distributed without a mannequin.

Various types of mannequins can be used, so long as the mannequin provides an opportunity to monitor at least some of the parameters discussed herein. In system 100, for example, the system includes a mannequin 200. Mannequin 200 is a model of a newborn infant's head 202. The head 202 includes a face 204 featuring a nose and mouth area that is sized and shaped to model the nose and mouth area of a newborn, and is preferably to scale.

Components in accordance with the invention can be manufactured and distributed as parts of a kit for teaching and practicing rescue breathing techniques. One example of a kit includes a mannequin 200 in combination with a bag-valve mask 120. The present invention is not limited solely to systems and kits, however. Other embodiments of the invention are directed exclusively to bag-valve masks as described herein. Still other embodiments are directed exclusively to mannequins as described herein. Therefore, the present invention is directed not only to the systems described herein, but also to the individual components described herein.

Pressure transducers in accordance with the invention can be configured in several ways. For example, the pressure transducers can be built directly into the mask. Alternatively, the pressure transducers can be located in a separate sheet or film that is placed over the nose and mouth area of a patient or mannequin. In systems where only a mannequin is used, the pressure transducers can be fixed on a surface of the mannequin itself. In system 100, for example, there are six pressure transducers 142 attached around the nose and mouth area of mannequin 200. Pressure transducers 142 are arranged in a spaced configuration around the nose and mouth area to measure mask pressure at six different zones. As will be explained, pressure measurements at the six different zones allow a clinician to monitor mask pressure around the nose and mouth and quickly identify any area of the mask that is not adequately sealed against the mannequin.

Transducers in accordance with the invention can be positioned on the mask, as opposed to the mannequin, as noted above. For example, transducers 142 can be attached to a cup portion 122 of mask 120 where the mask attaches to the face of the patient or mannequin. In this arrangement, the solid ovals representing transducers 142 in FIG. 1 would appear on cup portion 122 of mask 120, instead of on the face 204 of mannequin 200.

Systems in accordance with the invention also preferably include a sensor to monitor volumes of gas ventilated into and out of the mask. For example, mask 120 includes a third sensor 150 for measuring an inspiratory tidal volume $TV_i$ through the mask, and an expiratory tidal volume $TV_e$ through the mask. A measurement of $TV_i$ below a certain threshold can signal insufficient positive pressure applied by the clinician. A measurement of $TV_e$ that is less than the corresponding measurement of $TV_i$ can signal a leak and insufficient seal between the mask and patient, or between the mask and mannequin. The difference between $TV_e$ and $TV_i$ can be used to quantify a percentage leakage. The percent leakage, like all of the other parameters described herein, can be displayed by processor 180 on display monitor 190 to alert the clinician that a problem exists, and where the problem is located.

Systems in accordance with the invention also preferably include a sensor to monitor airway pressure, or $P_{aw}$, in the mask. For example, system 100 includes a fourth sensor 160 that measures peak inspiratory pressure (PIP) and positive end expiratory pressure (PEEP). Measurements of PIP and PEEP can each be compared against desired ranges. For example, a measurement of PIP that exceeds the maximum value in the desired range for PIP can signal that too much positive pressure is being applied that could injure a patient. A measurement of PEEP below the minimum value in the desired range for PEEP can signal insufficient gas exchange taking place.

Receiver 170 can be configured to receive measurements from sensors 130, 140, 150 and 160, and forward data to processor 180. Processor 180 can be configured to display the measurements and/or deliver an alarm signal in response to any measurement. As noted above, display monitor 190 can display measurements in real time to help the clinician monitor the various parameters that could indicate a problem. Processor 180 is programmed to display data in an easy to read format with visual and audio signals that allow the clinician to readily detect a problem, locate the cause or source, and correct the problem.

FIGS. 2-10E show various examples of screen shots, or sections of screen shots, that can be generated by processor 180 for display on display screen 192. These screen shots represent examples of screen layouts for conveying information to the clinician, and are not intended to limit the type of information conveyed to the clinician or limit the arrangement or appearance of information.

Figure 2:
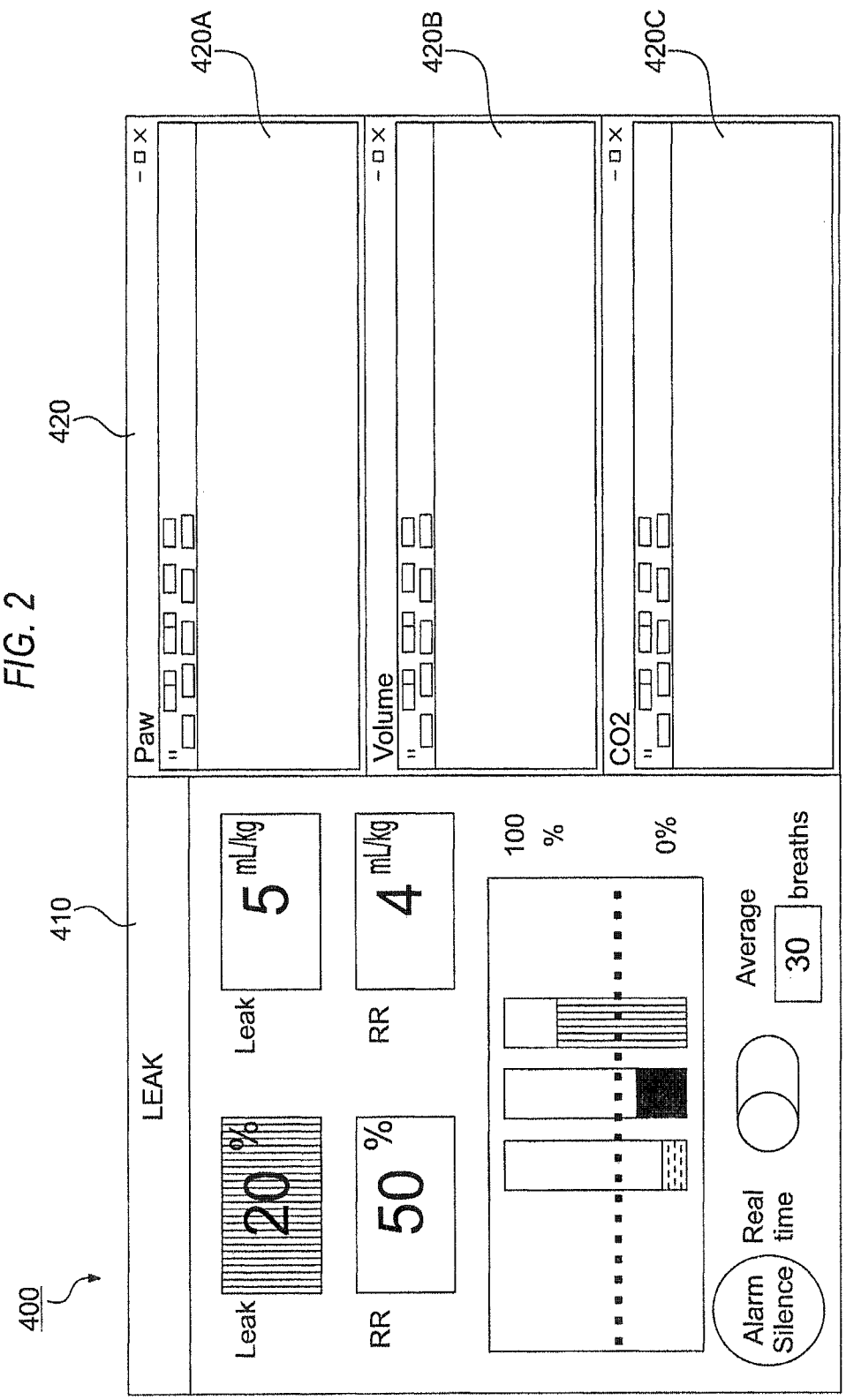
FIG. 2 is a schematic of a first display screen in accordance with an exemplary embodiment.

FIG. 2 shows a first exemplary screen shot 400. Screen shot 400 includes a left side 410 containing data relevant to the integrity of the mask seal. This data includes data for $TV_i$, $TV_e$, leak percentage and respiration rate (RR). Each value is shown in large font in a separate field or box. In the example shown, sensor 150 has detected a $TV_i$ of 5 mL/kg and a $TV_e$ of 4 mL/kg. This indicates a difference or net loss of 1 mL/kg of volume, which equates to a leakage of 20 percent. In a typical procedure, this amount of leakage is unacceptable. The box at the top left of left side 410 contains the value for "Leak", or leakage percentage. This box is displayed with a red background (represented by the vertical hatching) to provide a visual signal to the clinician that there is a problem with leakage. This visual signal enables the clinician to not only know immediately that a problem exists, but also to know what the problem is.

FIG. 2 also includes a right side 420 containing space to continuously display real-time data for different parameters. These parameters can be selected by the clinician. For example, right side 420 contains three windows 420A, 420B and 420C. Each window can display data for a different parameter. Window 420A contains space for a waveform that displays measurements of airway pressure, $P_{aw}$, in real time. Window 420B contains space for a waveform that displays fluctuations in volume in real time. Window 420C contains space for a waveform that displays fluctuations in carbon dioxide concentration in real time. Windows 420A-420C can be moved up or down, interchanged, re-arranged, etc. by the clinician at any time to customize the display and focus on specific parameters.

Screen shot 400 includes both the left side 410 and right side 420 visible on one screen. It will be understood that the display can be modified and rearranged in a number of ways. For example, the screen need not display both the left side 410 and right side 420 side by side. The user may wish to view only one side at a time. In such cases, the display can be configured to display information on one side only, and provide a toggle button that allows the user to switch between views of the left side 410 and right side 420.

Figure 3:
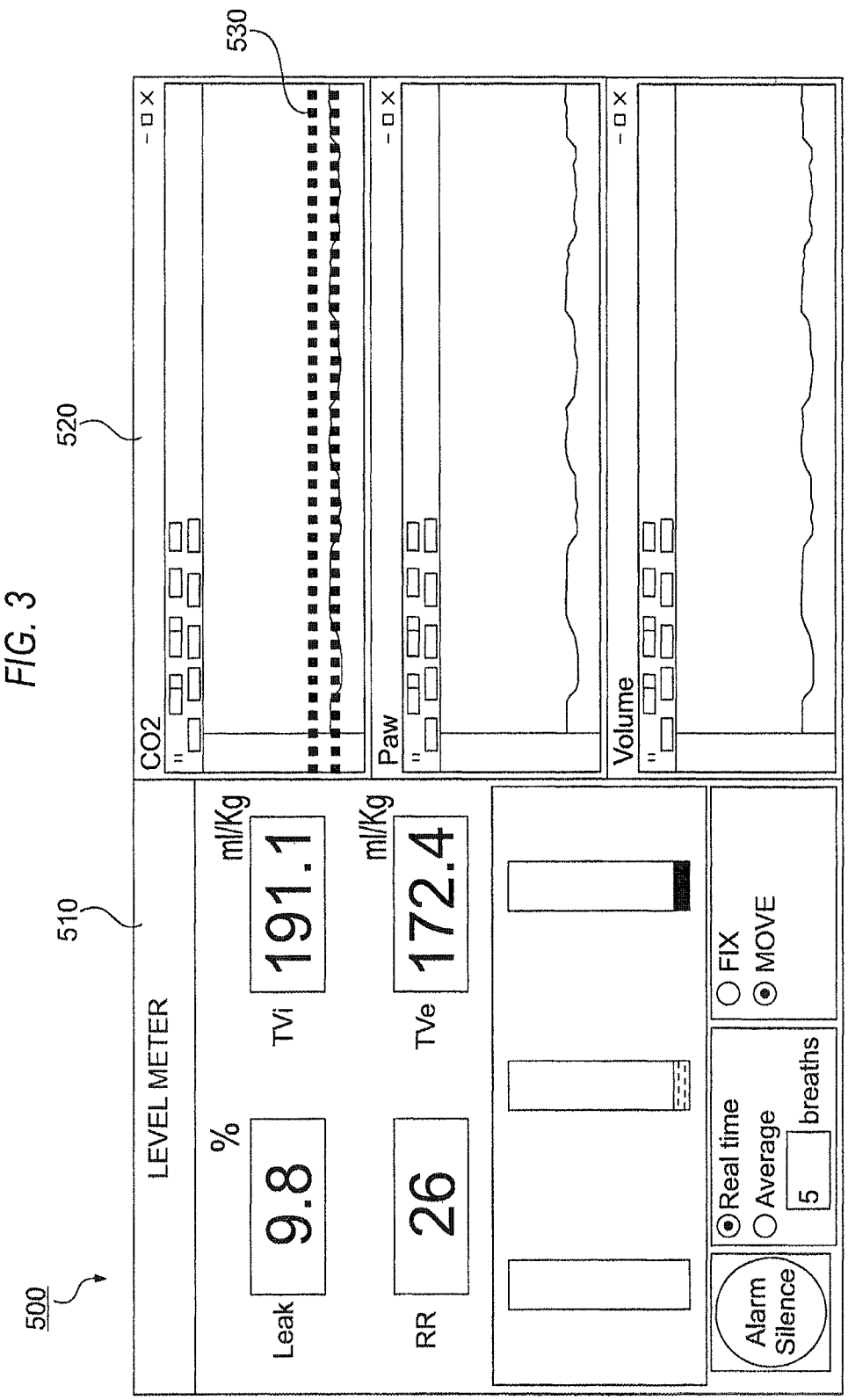
FIG. 3 is a schematic of a second display screen in accordance with an exemplary embodiment.

FIG. 3 shows another screen shot 500 with a left side 510 and right side 520 similar to left side 410 and right side 420 in FIG. 2. Left side 510 shows data for $TV_i$, $TV_e$, leak percentage and respiration rate (RR). Data for each parameter is shown in a separate box or field in the upper portion of the left side 510. Beneath these boxes, a graphical representation of the patient's last three breaths is shown. Each breath is represented by a rectangle, with the rectangles arranged from left to right according to sequence, with the earliest breath shown in the leftmost rectangle and the most recent breath shown in the rightmost rectangle. Each rectangle contains a bar that visually represents a leakage percentage, similar to a bar chart. In this example, the leakage percentage of the most recent breath was determined to be 9.8 percent, as shown in the upper left-hand box for "Leak". This amount of leakage is graphically shown by the black bar at the bottom of the rightmost rectangle.

Right side 520 of screen shot 500 contains three windows displaying waveform data. Proceeding from top to bottom, the windows display real-time data for carbon dioxide concentration, airway pressure and volume. The top window containing data for carbon dioxide concentration includes a pair of fixed dotted lines 530. Dotted lines 530 represent minimum and maximum desired levels for the end tidal concentration of carbon dioxide, $EtCO_2$. Thus, dotted lines 530 allow the clinician to readily see when $EtCO_2$ falls below or rises above the desired range. If desired, processor 180 and display unit 190 can be configured to alert the clinician when $EtCO_2$ falls below or rises above the desired range by using visual or audio signals to get the attention of the clinician. For example, the window corresponding to carbon dioxide concentration can flash, and/or display unit 190 can elicit an audio signal or alarm sound.

Figure 4:
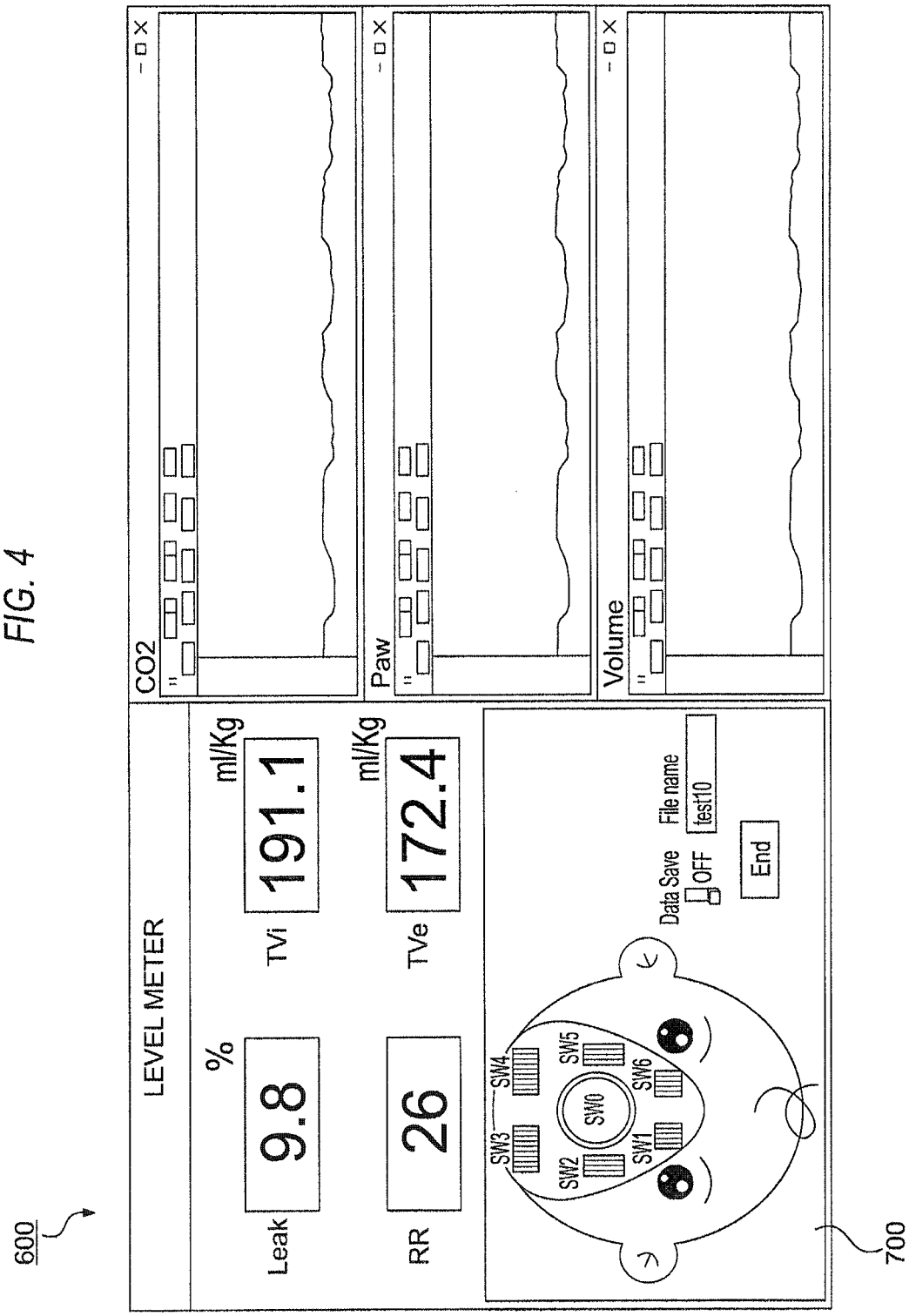
FIG. 4 is a schematic of a third display screen in accordance with an exemplary embodiment.
Figure 5:
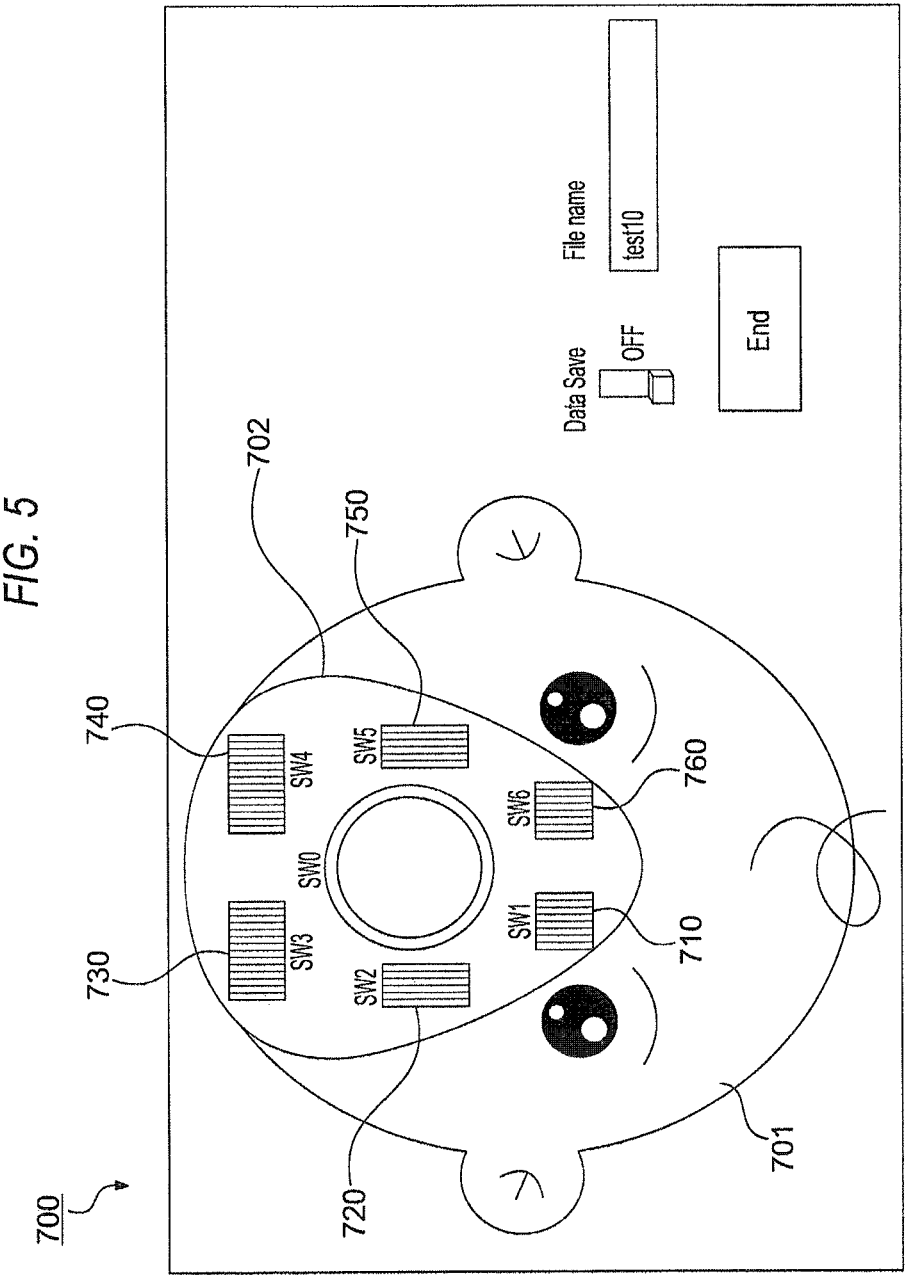
FIG. 5 is an enlarged view of one area of the third display screen of FIG. 6.

FIG. 4 shows a screen shot 600 that is similar in many respects to screen shot 500. One difference is that screen shot 600 includes a graphical display or "map" 700 of the six different zones around the nose and mouth of the patient or mannequin, where pressure is measured by pressure transducers 142. An enlarged view of map 700 is shown in FIG. 5.

As noted above, pressure transducers 142 are arranged in a spaced configuration around the nose and mouth area. One pressure transducer is located at each of the zones. Map 700 includes a cartoon illustration 701 representing the face of the patient or mannequin, and an outline 702 representing the footprint of the mask that covers the nose and mouth area. Map 700 also includes six blocks 710, 720, 730, 740, 750 and 760. Each block has a location relative to outline 702 that corresponds to the location of one of the zones around the nose and mouth where pressure is monitored.

Pressure transducers 142 send pressure measurements to the receiver 170, which forwards the data to processor 180. Processor 180 is programmed to inform the clinician of pressure conditions at each of the zones by utilizing visual indicia on map 700. For example, if the mask pressure at each of the zones is at an acceptable pressure, each of the blocks can be shown on display screen 192 as a solid green block. If the pressure at any of the zones falls below a threshold value representing an acceptable pressure, then the block corresponding to that zone changes to a solid red block. A solid red block anywhere on map 700 indicates that the mask pressure at the zone corresponding to that block is below the acceptable pressure, and that a leak is occurring at that location. This graphical feature allows the clinician to immediately learn when a mask leak occurs, identify the location of the leak, and take corrective action to seal the leak. Systems in accordance with the invention may utilize any color scheme or pattern to visually communicate the status at each zone. In addition, systems in accordance with the invention can utilize any number of audio signals or alarms in conjunction with map 700 to alert the clinician when a leak occurs.

In some instances, it may be desirable to monitor mask pressure and alert the clinician when too much mask pressure is being applied at any of the zones. In such instances, processor 180 and display unit 190 can be configured to communicate when any of the zones has a pressure measurement above a maximum threshold. For example, when too much pressure is applied at one zone, the block on map 700 corresponding to that zone can change color to a solid blue rectangle. In addition, an audio signal or alarm can alert the clinician that too much pressure is being applied at that location.

Figure 6:
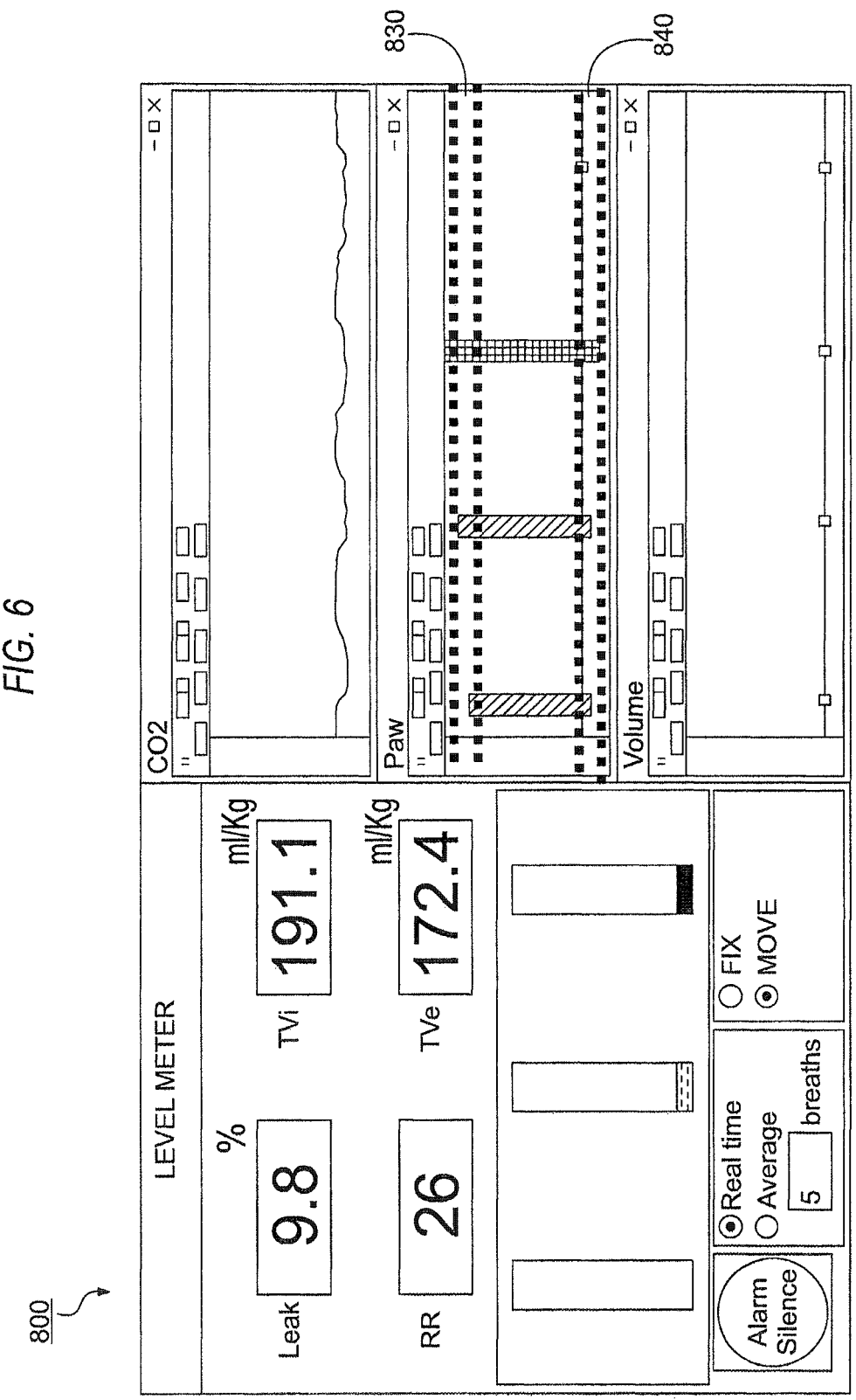
FIG. 6 is a schematic of a fourth display screen in accordance with an exemplary embodiment.

FIG. 6 shows another example of a screen shot 800 that is similar to screen shot 500 of FIG. 3. The right side of screen shot 800 includes a middle window that monitors airway pressure in real time. This window includes two pairs of fixed dotted lines, 830 and 840. Dotted lines 830 near the top of the window visually represent a desired range for PIP. Dotted lines 840 near the bottom of the window visually represent a desired range for PEEP. The pairs of dotted lines 830, 840 allow a clinician to readily see when PIP or PEEP fall outside the desired ranges. If desired, processor 180 and display unit 190 can be configured to alert the clinician when PIP or PEEP fall outside the desired ranges by using visual and/or audio signals to get the attention of the clinician. For example, the window corresponding to airway pressure can flash, and/or display unit 190 can elicit an audio signal or alarm sound.

Figure 7:
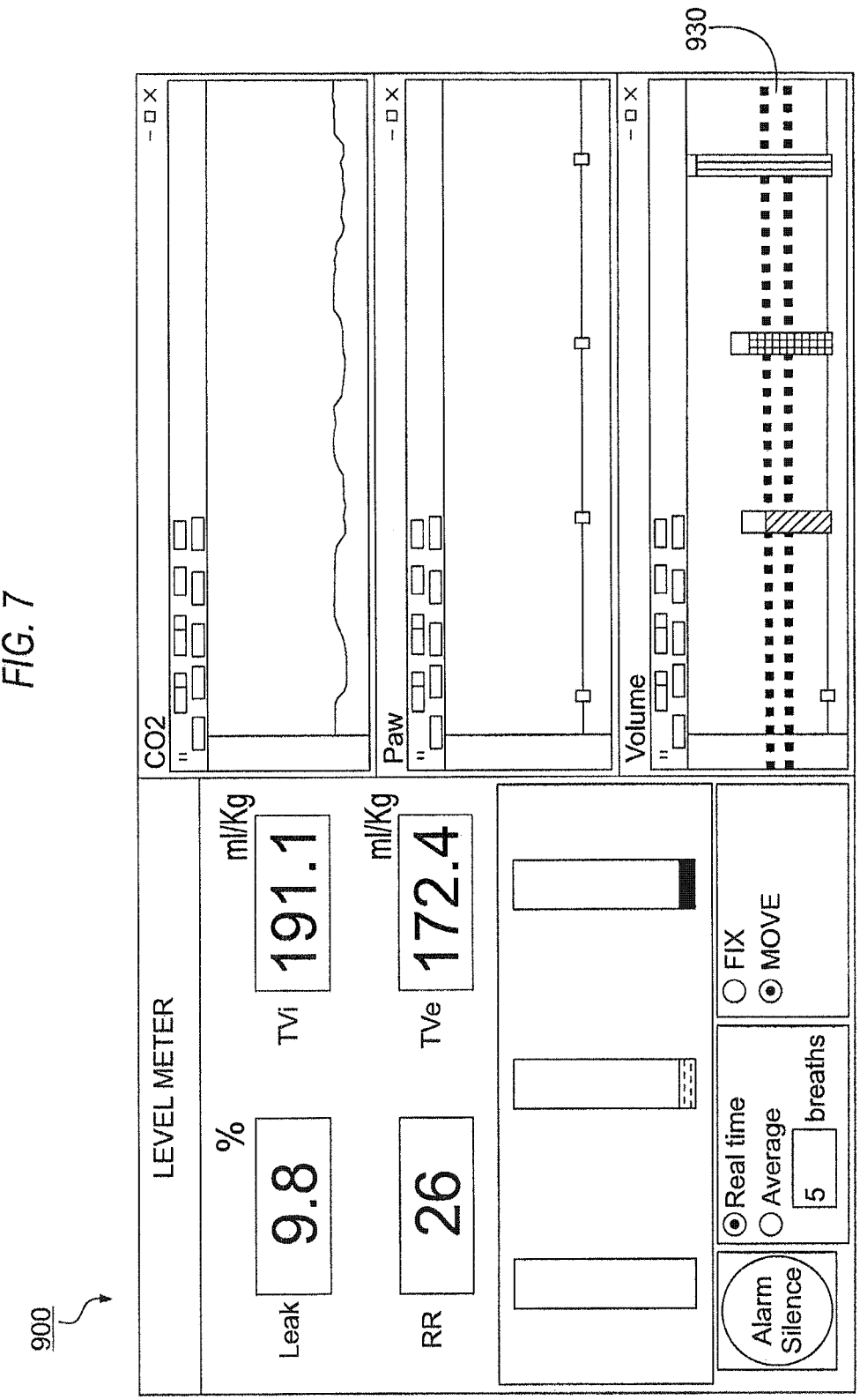
FIG. 7 is a schematic of a fifth display screen in accordance with an exemplary embodiment.

FIG. 7 shows another example of a screen shot 900 that is similar to screen shot 500 of FIG. 3. The right side of screen shot 900 includes a bottom window that monitors $TV_i$ and $TV_e$ in real time. This window includes a pair of fixed dotted lines 930. Dotted lines 930 visually represent a desired range for $TV_e$ and allow a clinician to immediately learn when $TV_e$ falls outside the desired range. In preferred embodiments, display unit 190 alerts the clinician when $TV_e$ is above the desired maximum threshold, and the extent to which the measured $TV_e$ exceeds the maximum threshold. In screen shot 900, for example, the window displays vertical bars. Each vertical bar corresponds to one breath, and displays the measurement for $TV_i$ and $TV_e$. If $TV_e$ falls within the desired range, for example between 4-6 mL/kg, then the bar is displayed as a green bar, with the color green representing an acceptable condition. If $TV_e$ is below the minimum threshold by a moderate amount, or above the maximum threshold by a moderate amount, for example between 3-4 mL/kg or 6-7 mL/kg, then the bar is displayed as a yellow bar, with the color yellow representing a condition of moderate concern. If $TV_e$ is below the minimum threshold by a significant amount, or above the maximum threshold by a significant amount, for example less than 3 mL/kg, or greater than 7 mL/kg, then the bar is displayed as a red bar, with the color red representing a condition of significant concern. The thresholds can be set or adjusted by the clinician. As with the other parameters, processor 180 and display unit 190 can be configured to alert the clinician when $TV_e$ falls outside of the desired range by using visual or audio signals to get the attention of the clinician. For example, the window corresponding to $TV_i$ and $TV_e$ can flash, and/or display unit 190 can elicit an audio signal or alarm sound. For this purpose, display unit 190 includes or is connected to an alarm unit 194. Alarm unit 194 can be in the form of the display screen of the display unit 190, a flashing light on or separate from the display unit, a speaker, and/or any other component configured to generate a visual signal, audio signal or other type of alarm.

Systems in accordance with the invention thus provide compact, inexpensive and easy-to-use systems for learning, practicing and performing proper rescue breathing techniques. System 100 provides an all-in-one apparatus for monitoring all of the critical parameters in a rescue breathing procedure. That is, system 100 can simultaneously monitor parameters including carbon dioxide concentration, airway pressure, $TV_i$, $TV_e$, leakage percentage and respiratory rate, all in real time. The display unit 190, which may be a conventional processor monitor, provides a large display as compared to conventional flow monitors with small built-in screens. The large display allows the clinician to monitor different parameters from as far away as 3 meters or farther, without having to leave a patient's side. The clinician can remain at a patient's side to administer positive pressure, and still be able to monitor several parameters at one time. This makes it much more feasible for a single person to perform an effective rescue breathing procedure when other personnel are not available to assist. The receiver can be made very small, and the sensors can be integrated with the mask, so that the system does not occupy significant space and can be easily implemented in an ER or NICU area.

Display units in accordance with the invention can use various cartoon images, symbols, emojis and other types of illustrations to visually convey various operating conditions in real time. These operating conditions include, but are not limited to, the integrity or "attachment condition" of the mask seal, and the patient's condition. For purposes of this description, the term "element" will be used to refer to a cartoon image, symbol, emoji or other type of illustration or indicia used to communicate a specific condition to medical personnel, medical trainees or other personnel using the system.

The processor 180 determines whether the mask 120 is in any one of three attachment conditions, and an image of an element representing the determined attachment condition is displayed in the screen 192. The images corresponding to the attachment conditions of the mask 120 which are determined by the processor 180 are shown in FIGS. 8A, 8B, 8C and 8D. Here, three examples of the attachment conditions of the mask 120 are described, however the attachment conditions of the mask are not limited to them.

If force with which the mask 120 presses against the patient or mannequin is weak, that is, air leaks from the mask 120, the image shown in FIG. 8A is displayed. In a case where a value acquired from a ventilatory (flow) sensor exceeds a preset threshold, the image shown in FIG. 8A is displayed. Specifically, it is preferable that the image is displayed when the relationship between V0 and V1 is abnormal. Here, V0 means a ventilatory volume in an inspiratory phase which is measured by the ventilatory (flow) sensor, and V1 means a ventilatory volume in a respiratory phase which is measured by the ventilatory (flow) sensor. The relationship between V0 and V1 is abnormal, for example, when a value obtained from (V0−V1)/V1*100[%] exceeds a preset threshold. The preset threshold can be 20% for example, or a higher or lower threshold. The determining method is not limited to this method.

If force with which the mask 120 presses against the patient or mannequin is appropriate, that is, air does not leak from the mask 120, the image shown in FIG. 8B is displayed. In a case where a value acquired from a ventilatory (flow) sensor is within a preset range, the image shown in FIG. 8B is displayed. It is preferable that the image is displayed when the relationship of V0 and V1 is normal.

If force with which the mask 120 presses against the patient or mannequin is too high, as for example where the mask exerts a force against the patient's face that is much higher than needed to ensure a good seal, the image shown in FIG. 8C is displayed. Moreover, in a case where a value acquired from a pressure sensor exceeds a preset threshold, the image shown in FIG. 8C is displayed. If a plurality of pressure sensors are provided, as shown in FIG. 8D, the image may indicate where the pressure is too high. FIG. 8D shows six blocked areas around the perimeter of the mask area that schematically represent and spatially correspond to six zones around the mask. One of the blocked areas on the right side of the mask area appears darker than the other blocked areas in FIG. 8D. This darker area represents an area having a different color, shading or pattern than the other areas to alert the user(s) that the pressure against the patient's face at the corresponding zone is too high.

The processor 180 further determines whether the human patient or the mannequin is in any one of three conditions, and an image of an element representing the determined condition is displayed in the screen 192. The images corresponding to the conditions of the human patient or the mannequin which are determined by the processor 180 are shown in FIGS. 9A, 9B and 9C. Here, three examples of the conditions of the human patient or the mannequin are described, however the conditions of the human patient or the mannequin are not limited to them.

If ventilation is not adequate, that is, the patient has difficulty breathing, the image shown in FIG. 9A is displayed. In a case where a value acquired from any one of a gas concentration sensor, a respiratory rate sensor, a respiratory pressure sensor, a ventilatory (flow) sensor, and a pressure sensor exceeds a preset threshold, or is otherwise considered unacceptable, the image shown in FIG. 9A is displayed. This can occur, for example, when the concentration of CO2 is higher than a threshold, when the respiratory rate is less than a threshold, when the respiratory rate is lower than a threshold, when the ventilatory volume is less than a threshold, or when the pressure is lower than a threshold. In such cases, the image shown in FIG. 9A is displayed.

If ventilation is adequate, that is, the patient does not have difficulty breathing, the image shown in FIG. 9B is displayed. In a case where a value acquired from any one of a gas concentration sensor, a respiratory rate sensor, a respiratory pressure sensor, a ventilatory (flow) sensor, and a pressure sensor is within a preset range, for example, the image shown in FIG. 9B is displayed.

If force with which the mask 120 presses against the patient or mannequin is too high, for example where the mask exerts a force against the patient's face that is much higher than needed to ensure a good seal, the image shown in FIG. 9C is displayed. In a case where a value acquired from a pressure sensor exceeds a preset threshold, the image shown in FIG. 9C is displayed.

The element representing the attachment condition of the mask 120 and the element representing the condition of the human patient or the mannequin can be concurrently displayed in such a manner that the elements are combined with each other. Hereinafter, some image examples are described that include a combination image where the element representing the attachment condition of the mask 120 is overlapped on the element representing the condition of the human patient or the mannequin. The image examples are shown in FIGS. 10A, 10B, 10C, 10D and 10E. In the image examples, the combination image of the mask and the human patient or the mannequin shows the state where the mask is attached on the human patient or the mannequin so as to cover the nose and mouth. However, the combination image is not limited to this state. The element representing the attachment condition of the mask 120 and the element representing the condition of the human patient or the mannequin may be concurrently displayed in such a manner that the elements are horizontally or vertically aligned without being overlapped with each other. For example, the condition of the patient or mannequin, and the condition of the mask attachment, can be represented by separate elements that are displayed side by side on a screen, or with one element on the top half of the screen and another element on the bottom half of the screen.

Figure 10A:
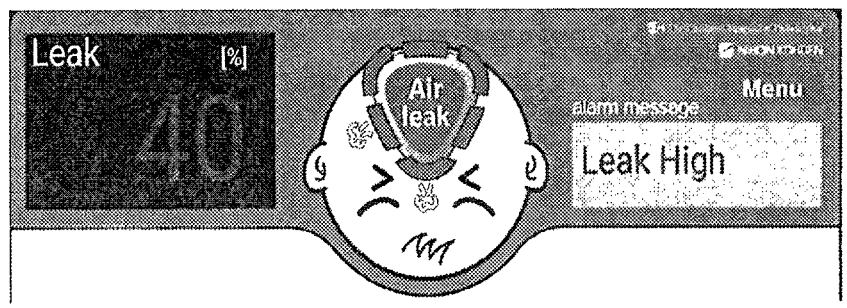
FIGS. 10A to 10E are view showing image examples including combination images of the attachment condition of the mask and the condition of the human patient or the mannequin.

If a leak amount based on data acquired from the ventilatory (flow) sensor exceeds an alarm setting value, the image example shown in FIG. 10A is displayed. In FIG. 10A, the image corresponding to the human patient or the mannequin indicates a difficult expression, such as when the patient is struggling or under duress. This image can signal, for example, that the patient is not breathing in enough oxygen due to excessive leakage from the mask. In the image corresponding to the mask, portions corresponding to the force sensors where output of the force sensors are equal to or lower than a setting value are colored with one color, for example, orange. In a case where the force sensors are not connected, all portions in the image are colored with another color, for example, green. The message, "Leak High" is displayed in the field of alarm message. FIG. 10A also includes other indicia resembling puffs of air to visually represent and convey that excessive leakage is occurring through the mask.

Figure 10B:
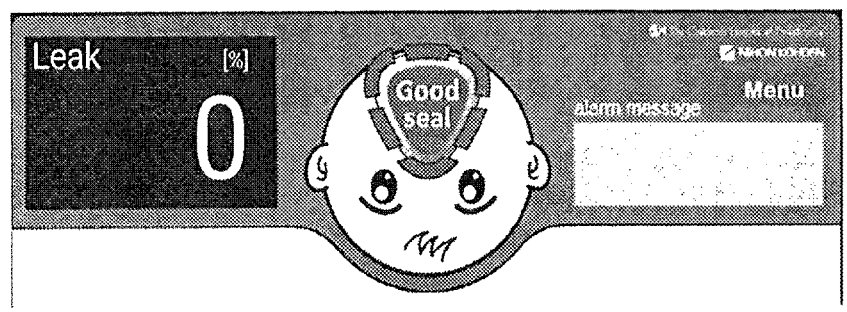

If the leak amount based on data acquired from the ventilatory (flow) sensor is equal to or lower than the alarm setting value, the image example shown in FIG. 10B is displayed. In FIG. 10B, the image corresponding to the human patient or the mannequin indicates a normal expression. In the image corresponding to the mask, all portions corresponding to the force sensors are colored with green. In a case where the force sensors are not connected, all portions in the image are colored with green.

Figure 10C:
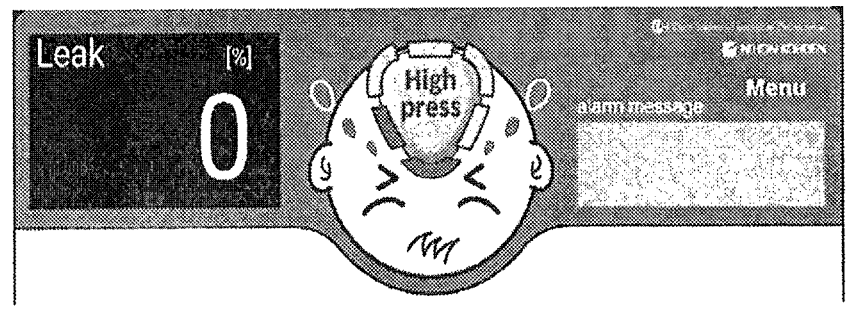
Figure 10D:
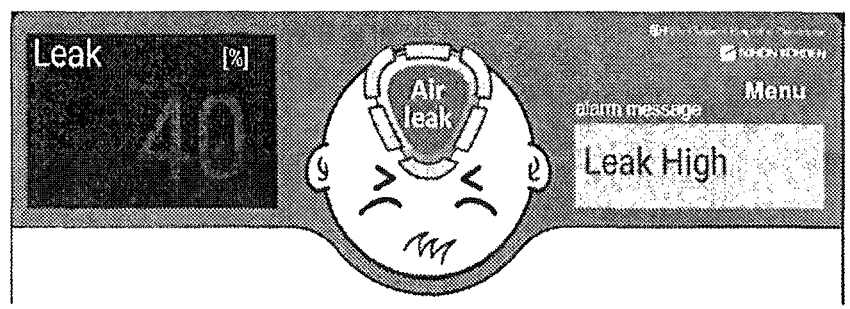

If the leak amount based on data acquired by the ventilatory (flow) sensor is equal to or lower than the alarm setting value, and the output of the force sensor exceeds the setting value, the image example shown in FIG. 10C is displayed. In FIG. 10C, the image corresponding to the human patient or the mannequin indicates a painful expression. In the image corresponding to the mask, portions corresponding to the force sensors where output of the force sensors exceed the setting value are colored with another color, for example, yellow. In a case where the force sensors are not connected, all portions in the image are colored with green. If the pressure sensors are not connected, the image corresponding to the mask with the message "High press" (FIG. 8C) is not displayed and the image corresponding to the mask with the message "Good seal" (FIG. 8B) is displayed. If the leak amount based on data acquired from the ventilatory (flow) sensor exceeds the alarm setting value, and the output of the force sensor exceeds a HIGH value of the setting value, the image example shown in FIG. 10D is displayed. In FIG. 10D, the image corresponding to the human patient or the mannequin indicates a painful expression. In the image corresponding to the mask, portions corresponding to the force sensors where output of the force sensors exceed the setting value are colored with yellow. The message, "Leak High" is displayed in the field of alarm message.

Figure 10E:
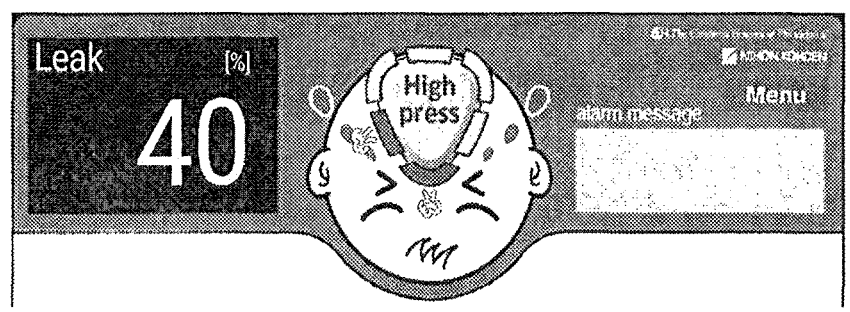

If the leak amount based on data acquired from the ventilatory (flow) sensor is equal to or lower than the alarm setting value, and the output of the force sensor exceeds a LOW value and the HIGH value of the setting value, the image example shown in FIG. 10E is displayed. In FIG. 10E, the image corresponding to the human patient or the mannequin indicates a painful expression. In the image corresponding to the mask, portions corresponding to the force sensors where output of the force sensors are equal to or lower than the setting value are colored with orange. Portions corresponding to the force sensors where output of the force sensors exceed the setting value are colored with yellow.

In the field of the alarm message, a message such as "Leak High", "High Volume", "Mask Leak" or the like can be displayed. In addition, the alarm message can include a suggested remedial action or instruction to address the adverse condition and end the alarm. For example, a message instructing a user to lift the patient's jaw or the like can be displayed.

While preferred embodiments of the invention have been shown and described herein, it will be understood that such embodiments are provided by way of example only. For example, systems in accordance with the invention can be, but need not be, an all-in-one system that monitors a number of different parameters like carbon dioxide concentration, airway pressure, TVi, TVe, leakage percentage and respiratory rate. Instead, the system can be designed to only monitor some of these parameters, depending on need. For example, some embodiments of the invention can be designed to monitor only mask pressure around the nose and mouth. Such an embodiment might be desired in a training context to focus solely on maintaining an air tight seal. Embodiments that only monitor some but not all parameters can be used alongside other equipment that monitors other parameters.

Numerous variations, changes and substitutions will occur to those skilled in the art without departing from the scope of the invention. Accordingly, it is intended that the appended claims cover all such variations, changes and substitutions.

What is claimed:
1. A system comprising:
a first sensor configured to measure one of a ventilatory volume, a concentration of gas, a respiratory rate and a respiratory pressure;
a second sensor configured to measure a pressure associated with a mask adapted to be attached to a human patient or a mannequin;
a processor configured to analyze a measurement value of the first sensor and a measurement value of the second sensor; and an output unit connected to the processor, the output unit configured to output, based on a result of the analysis of the processor:
a condition of the mask adapted to be attached to the human patient or the mannequin; and
a condition of the human patient or the mannequin,
wherein the output unit includes a display unit configured to display an image in which an element representing the condition of the mask is superimposed onto an element representing the condition of the human patient or the mannequin.

2. The system according to claim 1 further comprising an adapter to which the first sensor is attached.

3. The system according to claim 1, wherein the second sensor is located on the mask.

4. The system according to claim 1, wherein the second sensor is located on the mannequin.

5. The system according to claim 1 further comprising an alarm unit configured to output an alarm in accordance with the measurement value of the first sensor.

6. The system according to claim 5, wherein the output unit is configured to output an instruction when the alarm unit outputs the alarm.

7. The system according to claim 1 further comprising the mask which is attachable to the human patient or the mannequin.

8. A system comprising:
a first sensor configured to measure a first one of parameters including a ventilatory volume, a concentration of gas, a respiratory rate and a respiratory pressure;
a processor configured to analyze a measurement value of the first sensor; and
an output unit connected to the processor, and configured to output, based on a result of the analysis of the processor: a condition of a mask adapted to be attached to a human patient or a mannequin; and a condition of the human patient or the mannequin,
wherein the output unit includes a display unit configured to display an image in which an element representing the condition of the mask is superimposed onto an element representing the condition of the human patient or the mannequin.

9. The system according to claim 8 further comprising: a second sensor configured to measure a second one of the parameters, wherein
the first one of the parameters measured by the first sensor is different from the second one of the parameters measured by the second sensor, and
the processor is configured to analyze the measurement value of the first sensor and a measurement value of the second sensor.

10. The system according to claim 9 further comprising: a third sensor configured to measure a pressure associated with the mask adapted to be attached to the human patient or the mannequin, wherein
the processor is configured to analyze the measurement value of the first sensor, the measurement value of the second sensor, and a measurement value of the third sensor.

11. The system according to claim 10, wherein the third sensor includes a plurality of sensors arranged on a plurality of positions and configured to measure pressures at the plurality of positions, respectively, and
the output unit is configured to further output information related to the pressures of the plurality of positions.

12. The system according to claim 8 further comprising: a second sensor configured to measure a pressure associated with the mask adapted to be attached to the human patient or the mannequin, wherein
the processor is configured to analyze the measurement value of the first sensor and a measurement value of the second sensor.

13. The system according to claim 12, wherein the second sensor includes a plurality of sensors arranged on a plurality of positions and configured to measure pressures at each of the plurality of positions, respectively, and
the output unit is configured to further output information related to the pressures at each of the plurality of positions.

14. The system according to claim 9, wherein the first sensor is configured to measure the ventilatory volume, and
the image element representing the condition of the mask is obtained based on the ventilatory volume measured by the first sensor.

15. The system according to claim 8, wherein the element representing the condition of the human patient or the mannequin is obtained based on the first one of the parameters measured by the first sensor.

16. The system according to claim 12, wherein the first sensor is configured to measure the ventilatory volume, and
the element representing the condition of the mask is obtained based on the ventilatory volume measured by the first sensor or the pressure associated with the mask measured by the second sensor.

17. The system according to claim 12, wherein the element representing the condition of the human patient or the mannequin is obtained based on the first one of the parameters measured by the first sensor or the pressure associated with the mask measured by the second sensor.

18. A system comprising:
a first sensor configured to measure a first one of parameters including a ventilatory volume, a concentration of gas, a respiratory rate and a respiratory pressure;
a processor configured to analyze a measurement value of the first sensor; and
an output unit connected to the processor, and configured to output, based on a result of the analysis of the processor, at least one of: a condition of a mask adapted to be attached to a human patient or a mannequin; and a condition of the human patient or the mannequin,
wherein the output unit includes a display unit configured to display an image in which an element representing the condition of the mask and an element representing the condition of the human patient or the mannequin are overlapped with each other, and
wherein the display unit is configured to concurrently display:
a first image of the element representing the condition of the mask;
a second image of the element representing the condition of the human patient or the mannequin; and
a third image in which the element representing the condition of the mask is overlapped on the element representing the condition of the human patient or the mannequin.

* * * * *